US010646157B2

(12) United States Patent
Hallberg (10) Patent No.: US 10,646,157 B2
(45) Date of Patent: May 12, 2020

(54) SYSTEM AND METHOD FOR MEASURING BODY JOINT RANGE OF MOTION

(71) Applicant: Sharp Laboratories of America (SLA), Inc., Camas, WA (US)

(72) Inventor: Bryan Hallberg, Vancouver, WA (US)

(73) Assignee: Sharp Laboratories of America, Inc., Vancouver, WA (US)

(*) Notice: Subject to any disclaimer, the term of this patent is extended or adjusted under 35 U.S.C. 154(b) by 614 days.

(21) Appl. No.: 15/155,943

(22) Filed: May 16, 2016

(65) Prior Publication Data

US 2016/0324461 A1 Nov. 10, 2016

Related U.S. Application Data

(63) Continuation-in-part of application No. 15/091,869, filed on Apr. 6, 2016, now abandoned, which is a continuation-in-part of application No. 14/873,946, filed on Oct. 2, 2015, now Pat. No. 9,846,040, which is a continuation-in-part of application No. 14/742,852, filed on Jun. 18, 2015, now Pat. No. 10,352,725, and a continuation-in-part of application No. 14/707,194, filed on May 8, 2015, now Pat. No. 9,450,681.

(51) Int. Cl.
*A61B 5/00* (2006.01)
*A61B 5/11* (2006.01)

(52) U.S. Cl.
CPC .......... *A61B 5/4528* (2013.01); *A61B 5/1121* (2013.01); *A61B 5/742* (2013.01); *A61B 5/0024* (2013.01); *A61B 5/1114* (2013.01); *A61B 5/7475* (2013.01); *A61B 2562/0219* (2013.01)

(58) Field of Classification Search
CPC ..... A61B 5/4528; A61B 5/1121; A61B 5/742; A61B 5/0024; A61B 5/1114
See application file for complete search history.

(56) References Cited

U.S. PATENT DOCUMENTS

| | | | |
|---|---|---|---|
| 2003/0083596 A1* | 5/2003 | Kramer | A61B 5/1071 600/595 |
| 2012/0220904 A1 | 8/2012 | Warren | |
| 2014/0257142 A1 | 9/2014 | Sarkodie-Gyan et al. | |
| 2014/0316304 A2 | 10/2014 | Egen | |

* cited by examiner

*Primary Examiner* — Sean P Dougherty
(74) *Attorney, Agent, or Firm* — ScienBiziP, P.C.

(57) ABSTRACT

A system and method are provided for measuring body joint range of motion using inertial measurement unit (IMU) sensors capable of measuring their orientations relative to Earth. The method mounts a primary IMU sensor on a proximal body segment, and a secondary IMU sensor on a distal body segment connected to the proximal body segment via a joint. The sensor orientation relationship is measured between the primary IMU sensor and the secondary IMU sensor. In one aspect, the sensor orientation relationship is expressed as a quaternion. The sensor orientation relationship is converted into at least one physiologically modeled constituent joint rotation relationship between the proximal body segment and the distal body segment. More explicitly, the sensor orientation relationship is converted to a constituent axial axis, composite radial, or primary and secondary radial rotations of the distal body segment measured with respect to the proximal body segment.

8 Claims, 9 Drawing Sheets

Fig. 2E RIGHT SEGMENT ROTATES 20° INTO PAGE

| BODY SEGMENT | SENSOR ORIENTATION | SENSOR ID |
|---|---|---|
| HEAD | SOUTH | 0 |
| TRUNK UPPER | SOUTH | 1 |
| TRUNK LOWER | SOUTH | 2 |
| ARM UPPER LEFT | SOUTH | 3 |
| ARM UPPER RIGHT | SOUTH | 4 |
| FOREARM LEFT | EAST | 5 |
| FOREARM RIGHT | WEST | 6 |
| HAND LEFT | EAST | 7 |
| HAND RIGHT | WEST | 8 |
| THIGH LEFT | SOUTH | 9 |
| THIGH RIGHT | SOUTH | 10 |
| SHANK LEFT | SOUTH | 11 |
| SHANK RIGHT | SOUTH | 12 |
| FOOT LEFT | TOP | 13 |
| FOOT RIGHT | TOP | 14 |

| JOINT | DISTAL SEGMENT | PROXIMAL SEGMENT | AXIAL $\theta_a$ | RADIAL PRIMARY $\theta_{rp}$ | RADIAL SECONDARY $\theta_{rs}$ | AXIAL SIGN | RADIAL PRIMARY SIGN | RADIAL SECONDARY SIGN | AUTOMATIC ALIGNMENT | | |
|---|---|---|---|---|---|---|---|---|---|---|---|
| NECK | HEAD | TRUNK UPPER | | ROTATION LEFT ROTATION RIGHT | FLEXION EXTENSION | FLEXION EXTENSION | LATERAL LEFT LATERAL RIGHT | + + | - - | + + | PDM |
| BACK | TRUNK UPPER | TRUNK LOWER | | ROTATION LEFT ROTATION RIGHT | FLEXION EXTENSION | FLEXION EXTENSION | LATERAL LEFT LATERAL RIGHT | + + | - + | + - | PDM |
| SHOULDER LEFT | ARM UPPER LEFT | TRUNK UPPER | | MEDIAL ROTATION LATERAL ROTATION | FLEXION EXTENSION | FLEXION EXTENSION | ADDUCTION ABDUCTION | + - | + + | - + | PDM |
| SHOULDER RIGHT | ARM UPPER RIGHT | TRUNK UPPER | | MEDIAL ROTATION LATERAL ROTATION | FLEXION EXTENSION | FLEXION EXTENSION | ADDUCTION ABDUCTION | + + | + + | 0 0 | AP |
| ELBOW LEFT | FOREARM LEFT | ARM UPPER LEFT | | PRONATION SUPINATION | FLEXION EXTENSION | FLEXION EXTENSION | 0 | - 0 | + - | 0 0 | AP |
| ELBOW RIGHT | FOREARM RIGHT | ARM UPPER RIGHT | | PRONATION SUPINATION | FLEXION EXTENSION | FLEXION EXTENSION | 0 | 0 + | + + | - + | AP |
| WRIST LEFT | HAND LEFT | FOREARM LEFT | | 0 | FLEXION EXTENSION | FLEXION EXTENSION | RADIAL DEVIATION ULNAR DEVIATION | + - | - + | - + | AP |
| WRIST RIGHT | HAND RIGHT | FOREARM RIGHT | | 0 | FLEXION EXTENSION | FLEXION EXTENSION | RADIAL DEVIATION ULNAR DEVIATION | - + | + + | - + | PDM |
| HIP LEFT | THIGH LEFT | TRUNK LOWER | | MEDIAL ROTATION LATERAL ROTATION | FLEXION EXTENSION | FLEXION EXTENSION | ADDUCTION ABDUCTION | + - | + - | - + | PDM |
| HIP RIGHT | THIGH RIGHT | TRUNK LOWER | | MEDIAL ROTATION LATERAL ROTATION | FLEXION EXTENSION | FLEXION EXTENSION | ADDUCTION ABDUCTION | 0 0 | - 0 | 0 0 | AP |
| KNEE LEFT | SHANK LEFT | THIGH LEFT | | 0 | FLEXION EXTENSION | FLEXION EXTENSION | 0 | 0 0 | - - | 0 0 | AP |
| KNEE RIGHT | SHANK RIGHT | THIGH RIGHT | | 0 | FLEXION EXTENSION | FLEXION EXTENSION | 0 | - + | + + | - + | AP |
| ANKLE LEFT | FOOT LEFT | SHANK LEFT | | INVERSION EVERSION | DORSIFLEXION PLANTARFLEXION | DORSIFLEXION PLANTARFLEXION | ADDUCTION ABDUCTION | | | | AP |
| ANKLE RIGHT | FOOT RIGHT | SHANK RIGHT | | INVERSION EVERSION | DORSIFLEXION PLANTARFLEXION | DORSIFLEXION PLANTARFLEXION | ADDUCTION ABDUCTION | | | | AP |

SYSTEM AND METHOD FOR MEASURING BODY JOINT RANGE OF MOTION

BACKGROUND OF THE INVENTION

1. Field of the Invention

This invention generally relates to human body joint motion evaluation and, more particularly, to a system and method for converting inertial measurement unit (IMU) sensor measurements into physiologically defined joint rotation measurements in a standard format more easily understood by health care professionals.

2. Description of the Related Art

Measuring a body joint's range of motion (RoM) is critical for applications such as joint surgery recovery and sports technique coaching. It is also important for orthopedic patients to begin flexing the repaired joint soon after surgery is completed. Often the patient does not understand or correctly comply with the doctor's recovery instructions, and upon returning to their home, the patient is not sufficiently monitored by medical staff to determine if recovery is proceeding well. This lack of monitoring may result in poor RoM and the need for additional surgeries. It would also be advantageous to monitor range of motion dynamically, during normal daily activities. Many existing systems only measure statically, when the user is still and focused specifically on the measurement process.

Currently existing systems do not use physiologically modeled joint rotation decomposition to determine constituent joint rotations. They also are only capable of displaying a single planar rotation, and cannot calculate or display each of the constituent rotations that makeup the composite rotation. They require trained professionals to perform the measurement. They do not automatically adapt their analysis to the specific joints that are being measured. They do not show trending over time during normal daily usage. They are not able to send trending information to remote viewers. Many existing systems only measure statically, when the user is still and focused specifically on the measurement process.

It would also be advantageous to monitor range of motion dynamically, during normal daily activities, and present the measurements in an intuitive, easy to understand format.

SUMMARY OF THE INVENTION

The system described herein provides a method for measuring the range of motion of body joints when the body segments connected by the joint have an inertial measurement unit (IMU) attached to them reporting the orientation of the IMU relative to a reference object which emits gravitational and magnetic fields, such as Earth. This system provides an easy to use method to dynamically measure a user's range of motion and report the results back to medical staff or other interested parties for monitoring. The user interface adapts to the specific joint being measured. Results are based upon physiologically modeled quaternion joint rotation decomposition for superior stability and medically physiological relevancy, particularly when compared to Euler angles, yet the presentation is still intuitive and easily understood by both medical personnel and patients.

The system receives body segment spatial orientation vectors real-time from a pair of sensors attached to adjoining body segments, calculates the rotation of the intersecting joint, separates the joint rotation into constituent rotations, and displays the results both numerically and graphically. The user interface enables users to review the status of the sensors, assign sensors to the desired body segments, and select the joint whose range of motion will be monitored. From the joint selection, the system automatically determines the associated distal and proximal body segments and adjusts the display contents to the relevant metrics for the selected joint.

The display metrics may include a numerical readout, a dial readout, and a long term trending readout of each rotation of relevance for the target joint. The readouts include user definable, temporally adjusting, limits and targets for joint range of motion to clearly indicate to the user if they are approaching their joint rotation targets or exceeding their limits. The system can run on a personal computer (PC), smartphone, or smart tablet. Data can be transferred to the worldwide web for viewing by remote parties.

Accordingly, a method is provided for measuring body joint range of motion using IMU sensors capable of measuring their orientations relative to Earth. The method mounts a primary IMU sensor on a proximal body segment, and a secondary IMU sensor on a distal body segment connected to the proximal body segment via a joint. The sensor orientation relationship is measured between the primary IMU sensor and the secondary IMU sensor. In one aspect, the sensor orientation relationship is expressed as a quaternion. The sensor orientation relationship is converted into at least one physiologically modeled constituent joint rotation relationship between the proximal body segment and the distal body segment. A constituent joint rotation relationship is defined in no more than two dimensions of three-dimensional space. More explicitly, converting the sensor orientation relationship into the physiologically modeled constituent joint rotation relationship includes defining a constituent axial axis rotation of the distal body segment measured with respect to the proximal body segment. An axial axis intersects the joint connecting the distal body segment to the proximal body segment and is parallel to a major axis of a smallest rectangular cuboid enclosing a body segment. A major axis is defined as a line passing through the center of two opposing sides of the cuboid that are farthest apart from each other.

In one aspect, the sensor orientation relationship conversion defines a constituent radial axis composite rotation of the distal body segment measured with respect to the proximal body segment. The radial axis intersects the joint connecting the distal body segment to the proximal body segment, is orthogonal to an axial axis of the distal body segment, and is orthogonal to an axial axis of the proximal body segment. In another aspect, the radial axis composite rotation defines a constituent primary radial rotation and a constituent secondary radial rotation. The primary radial rotation represents a first angle measured with respect to a first axis aligned with the radial axis of maximum possible physiologically possible radial rotation. The secondary rotation represents a second angle measured with respect to a second axis orthogonal to the first axis and the axial axis.

The method may display the physiologically modeled constituent joint rotation relationship between the proximal body segment and the distal body segment, show the constituent joint rotation relationship as a numerical value representing an extent of rotation, or map at least one constituent rotation relationship to a physiologically defined joint rotation.

Additional details of the above described method, a system for measuring body joint range of motion using IMUs, and an associated graphic user interface (GUI) are presented below.

DETAILED DESCRIPTION

The systems and methods described herein use the notation, concepts, and techniques described in the following applications, which are incorporated herein by reference:

Ser. No. 14/873,946, entitled, SYSTEM AND METHOD FOR DETERMINING THE ORIENTATION OF AN INERTIAL MEASUREMENT UNIT (IMU), filed Oct. 2, 2015;

Ser. No. 15/091,869, entitled, SYSTEM AND METHOD FOR DETERMINING ORIENTATION OF BODY SEGMENTS USING INERTIAL MEASUREMENT UNITS, filed Apr. 6, 2016;

Ser. No. 14/742,852, SENSOR CALIBRATION METHOD AND SYSTEM, filed Jun. 18, 2015; and, Ser. No. 14/707,194, METHOD AND SYSTEM FOR WIRELESS TRANSMISSION OF QUATERNIONS, filed May 8, 2015.

Figure 1:
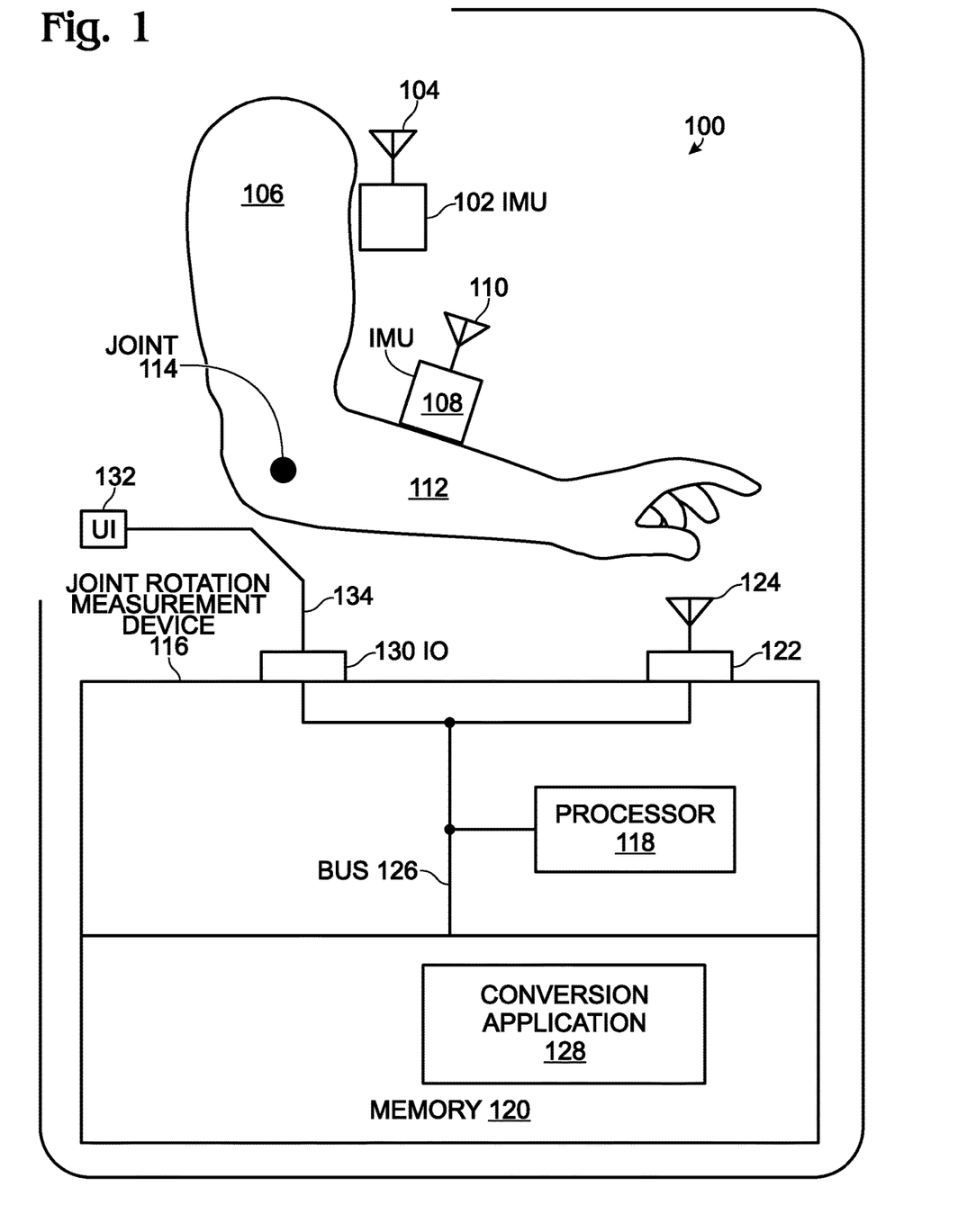
FIG. 1 is a schematic block diagram of system for measuring body joint range of motion using inertial measurement unit (IMU) sensors capable of measuring their orientation relative to Earth.

FIG. 1 is a schematic block diagram of system for measuring body joint range of motion using inertial measurement unit (IMU) sensors capable of measuring their orientation relative to Earth. The system 100 comprises a primary IMU sensor 102, having a wireless interface 104, mounting on a proximal body segment 106. A secondary IMU sensor 108 has a wireless interface 110, and is mounted on a distal body segment 112 connected to the proximal body segment 106 via a joint 114. As shown in this figure, the upper arm is the proximal body segment 106 and the forearm is the distal body segment 112.

A joint rotation measurement device 116 comprises a processor 118, a non-transitory memory 120, a communication module 122 having a wireless interface 124 to communicate with the primary IMU sensor 102 and secondary IMU sensor, and an internal interface, which may be a data/address bus 126 if all the elements are co-located. A conversion application 128 is connected to the internal interface 126, and is enabled as a sequence of processor executable instructions, and stored in the memory 120. The conversion application 128 measures the sensor orientation relationship between the primary IMU sensor 102 and the secondary IMU sensor 108, and converts the sensor orientation relationship to supply, via input/output (IO) 130, physiologically modeled constituent joint rotation relationship data describing the relationship between the proximal body segment 106 and the distal body segment 112. Typically, the conversion application 128 measures the sensor orientation relationship by expressing the sensor orientation relationship as a quaternion. A constituent joint rotation relationship is defined in no more than two dimensions of three-dimensional space, and is explained in greater detail below.

As shown, the IMU outputs are enabled as wireless devices, however, in some circumstances the output may be a hardwired or be an optical interface. The figure also implies that the processor 118, memory 120, and conversion application 128 reside in an external device—the joint rotation measurement device 116. For example, the joint rotation measurement device 116 may be a smartphone, personal computer, or stand-alone device. However, in some aspects, some or all of the elements of the processor 118, memory 120, and conversion application 128 reside in an IMU or in a network-connected server or database.

Figure 2A:
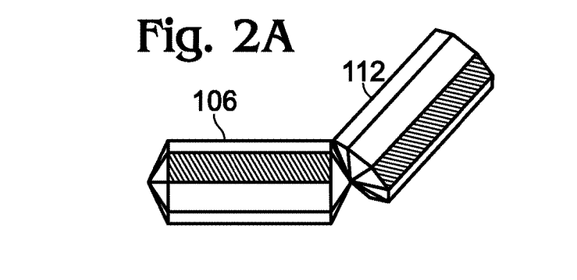
FIGS. 2A through 2E are figures defining joint composite and constituent rotation relationships.

FIGS. 2A through 2E are figures defining joint composite and constituent rotation relationships. In FIG. 2A, the relationship between the proximal body segment and distal body segment 112 can be understood as quaternion. A quaternion is a 4-element vector (r, x, y, z) based on rotation angle θ and unit length rotation axis $\vec{u}$. A quaternion that rotates an object from spatial coordinate system A to spatial coordinate system B is defined as the normalized vector $_A^B Q$.

$$_A^B Q = (r, x, y, z) = r + \hat{i}x + \hat{j}y + \hat{k}z$$
$$\hat{i}^2 = \hat{j}^2 = \hat{k}^2 = \hat{i}\hat{j}\hat{k} = -1$$
$$r = \cos\left(\frac{\theta}{2}\right); x = u_x \sin\left(\frac{\theta}{2}\right); y = u_y \sin\left(\frac{\theta}{2}\right); z = u_z \sin\left(\frac{\theta}{2}\right)$$
$$r^2 + x^2 + y^2 + z^2 = 1.$$

In this example,
J=joint Composite Rotation
$\hat{u}$=(0.67, 0.48, 0.56)
θ=57.8°.

While the joint composite rotation is accurate, its format is non-conventional in the medical field, and is better understood when broken down into sub-components or constituent rotation relationships.

Figure 2B:
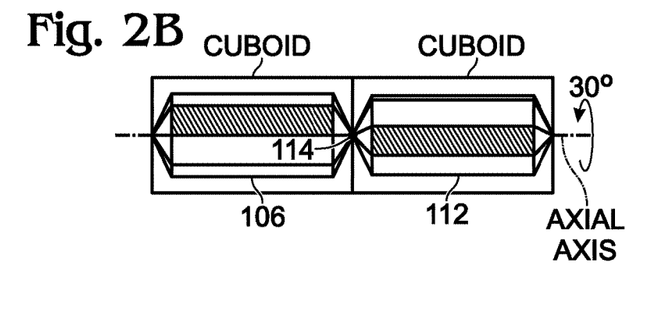

As shown in FIG. 2B, in one aspect the conversion application supplies data defining a constituent axial axis rotation of the distal body segment 112 measured with respect to the proximal body segment 106. An axial axis intersects the joint connecting the distal body segment to the proximal body segment and is parallel to a major axis of a smallest rectangular cuboid enclosing a body segment. The major axis is a line passing through the center of two opposing sides of the cuboid that are farthest apart from each other. In this case, the axial axis and major axes of both body segments are aligned together, so the major axis is not labeled. The methods disclosed herein assign the axial axis to the Y-axis.

In this example:
$J_y$=Constituent Axial Rotation
$\hat{u}$=(0, 1, 0)
θ=30°.

Figure 2C:
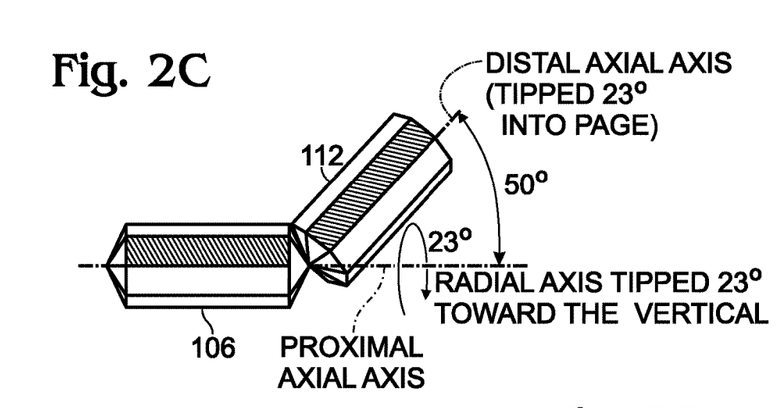

In FIG. 2C the conversion application supplies data defining a constituent radial axis composite rotation of the distal body segment measured with respect to the proximal body segment. The radial axis intersects the joint 114 connecting the distal body segment 112 to the proximal body segment 106, is orthogonal to an axial axis of the proximal body segment, and is orthogonal to an axial axis of the distal body segment.

In this example:
$J_{zx}$=Constituent Radial Composite Rotation
$\hat{u}$=(0.91, 0, 0.42)
$\theta$=50°.

Figure 2D:
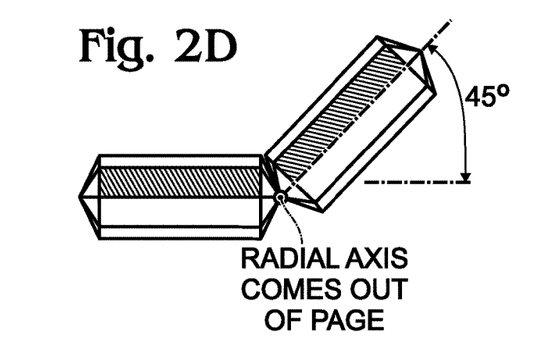
Figure 2E:
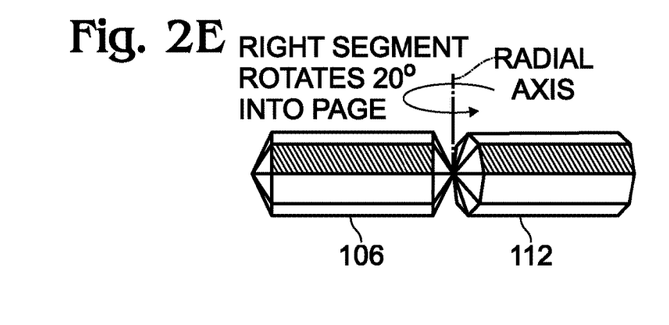
Figure 3A:
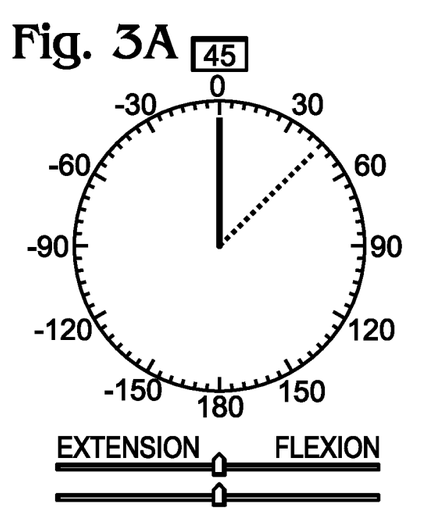
FIG. 3 depicts meters or dials measuring physiologically modeled constituent joint rotation relationships as a numerical value representing an extent of rotation.
Figure 3B:
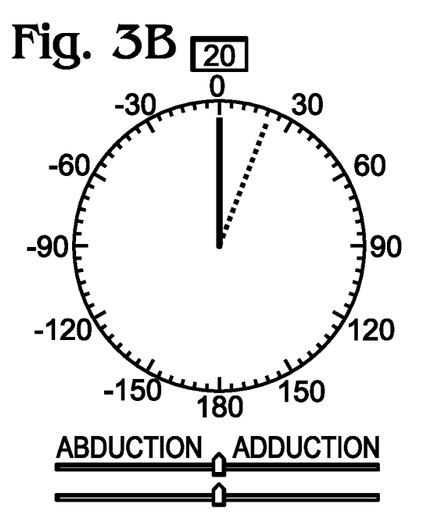
Figure 3C:
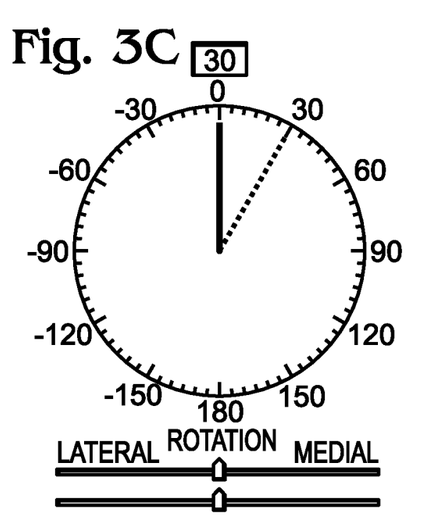
Figure 3D:
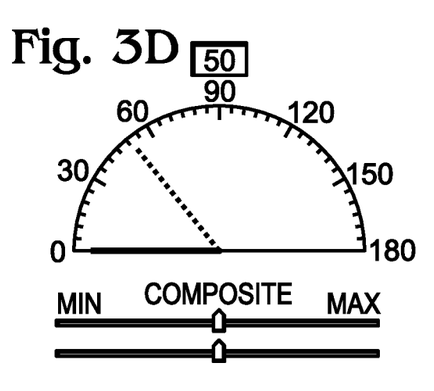

As an alternative to the constituent radial composite rotation, the conversion application may supply data defining a constituent primary radial rotation (FIG. 2D) and a constituent secondary radial rotation (FIG. 2E). The primary radial rotation represents a first angle measured with respect to a first axis aligned with the radial axis of maximum possible physiologically possible radial rotation. The methods disclosed herein assign this first axis to the X-axis.

The fact that in this example the joint also happens to be currently bent the most in the axis of maximum possible radial rotation is just by chance. For example, imagine the neck "joint". The head can move the most in the forward direction, compared to tipping to the side. So, the primary radial axis of neck joint goes from one shoulder to the other. The secondary goes from the back of the neck to the front. Even if a person only tips their head to the side, and not forward or back, the primary axis still goes from one shoulder to the other, independent of how they currently have their head tipped.

In this example:
$J_x$=Constituent Radial Primary Rotation
$\hat{u}$=(1, 0, 0)
$\theta$=45°.

The secondary rotation represents a second angle measured with respect to a second axis orthogonal to the first axis and the axial axis. The methods disclosed herein assign this second axis to the Z-axis. In this example:
$J_z$=Constituent Radial Secondary Rotation
$\hat{u}$=(0, 0, 1)
$\theta$=20°.

Returning to FIG. 1, a user interface (UI) 132, such as a display, is typically connected to the conversion application 128 on line 134, via IO 130, to display information representing the physiologically modeled constituent joint rotation relationship between the proximal body segment and the distal body segment. For example, the physiologically modeled constituent joint rotation relationships may be depicted with the three-dimensional cylindrical objects shown in FIGS. 2B-2E, or in the shape of a realistic human looking avatar. The UI 132 may also incorporate a touchscreen with selectable menus, keyboard, mouse, joystick, cursor control device, trackball, stylus, cursor direction keys, or accept voice commands, that permit a user to enter selections and commands.

The IO port 130 may incorporate a modem, an Ethernet card, or any other appropriate data communications device such as USB. The physical communication links may be optical, wired, or wireless. The joint rotation measurement device 116 may be considered a type of special purpose computing system, and as such, can be programmed, configured, and/or otherwise designed to comply with one or more networking protocols.

The joint rotation measurement device 116 may provide a direct connection to a remote server via a direct link to a network, such as the Internet. Connection may be provided through, for example, a local area network (such as an Ethernet network), a personal area network, a wide area network, a private network (e.g., a virtual private network), a telephone or cable network, a cellular telephone connection, a satellite data connection, or any other suitable connection.

FIG. 3 depicts meters or dials measuring physiologically modeled constituent joint rotation relationships as a numerical value representing an extent of rotation. These meter or dial readouts may be presented by the UI of FIG. 1 as an alternative, or in addition to the depiction of actual body segments. Using neck rotations as an example, then the proximal body segment is the upper chest, and the distal body segment is the head. In this case, using medical terminology, meter A describes the neck's flexion and extension, meter B describes the neck's lateral bending, meter C describes the neck's rotation, and meter D describes the neck's combined flexion, extension, and lateral bending.

Figure 4:
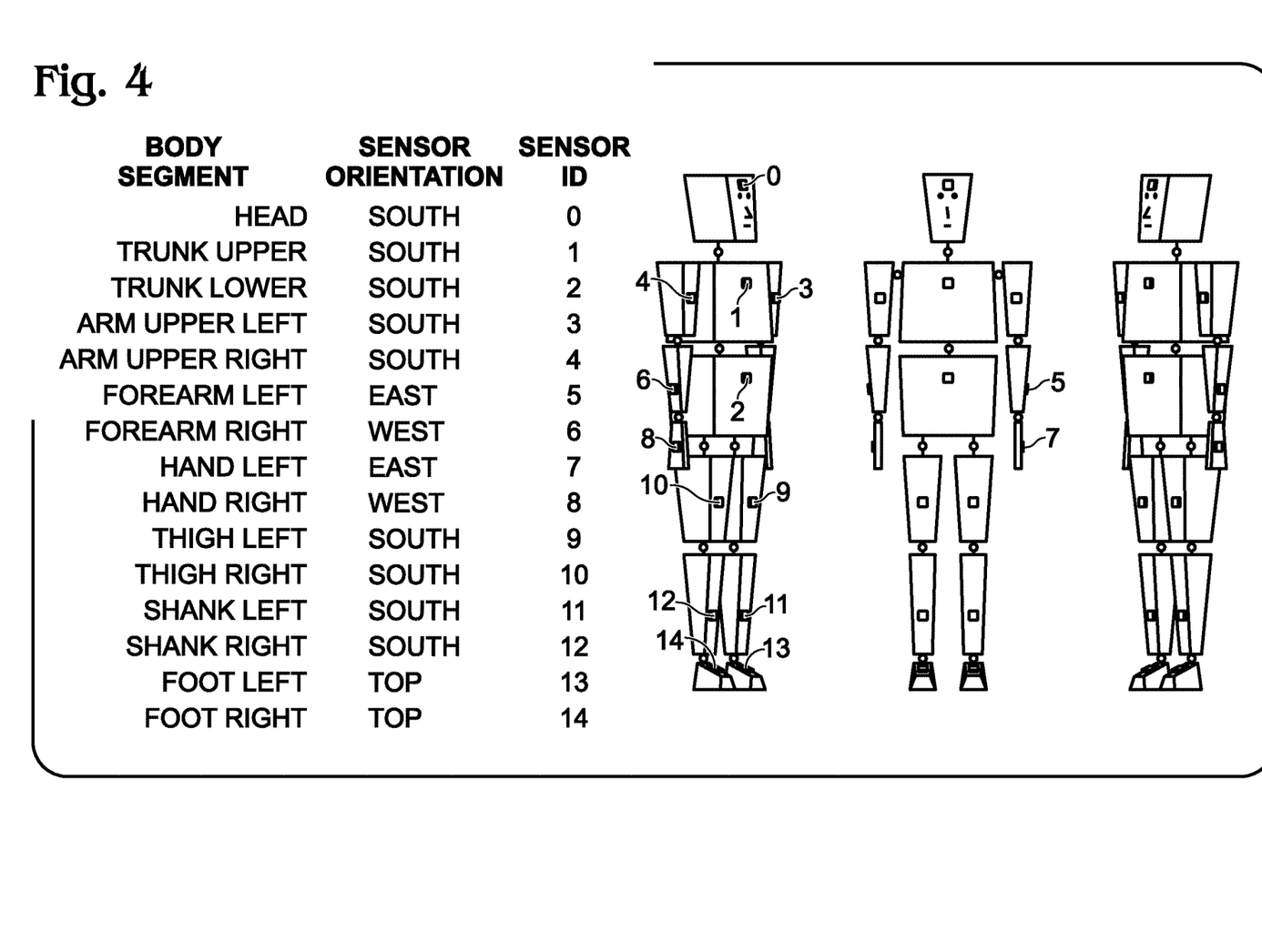
FIG. 4 depicts exemplary reference sensor orientations.

FIG. 4 depicts exemplary reference sensor orientations. An explanation of determining body segment orientations from IMUs attached to those body segments can be found in parent application Ser. No. 15/091,869. Since the relationship between adjoining body segments is expressed as constituent rotation relationships, it becomes relatively easy to select orientations and viewing angle, which can be graphical represented, based on the selection of the distal body segment. This data permits the display of joint angular rotations in short and long term trending representations, or the temporary setting of joint rotation targets and limits. The system permits the viewing of the connection and calibration status of sensors, assigns sensors to a particular body segment, and initiates the calibration of sensors. Sensors can be identified by representing sensor orientations with corresponding avatar body segment orientations. The system also permits sending a message to a sensor instructing it to blink its status LED to aid in identifying which sensor is associated with which body segment. The conversion application may erase current history data from the display, initiate sensor alignment, and then begin displaying newly received joint rotations again.

A quaternion representation of the joint rotation is derived from adjoining distal and proximal body segment orientations using the following equations.

$$_p{}^dJ = B'_p B_d = \text{joint rotation between distal and proximal segments}$$

$B_d$=distal segment orientation
$B_p$=proximal segment orientation

To compensate for joint rotation calculation offsets that are caused by adjoining body segments having dissimilar reference sensor orientations (such as the elbow joint), the reference sensor offsets are removed from the body segment orientations before the joint rotation calculation by rotating them by the inverse of their reference sensor pose orientations.

$$J_{pc} = (_E{}^P B'_p B_p)'(_E{}^P B'_d B_d) = B'_{pE}{}^P B_{pE}{}^P B'_d B_d$$

$J_{pc}$=pose compensated joint rotation
$_E{}^P B_p$=proximal body segment pose orientation
$_E{}^P B_d$=distal body segment pose orientation The pose compensated joint rotation is then positive definite adjusted about its r dimension to obtain the composite joint rotation of the distal body segment relative to the proximal body segment.

$$J = \text{PosDef}(r, J_{pc})$$

In general, the joint composite rotation J does not have any physiologically meaningful interpretation. The axis of rotation does not align with any body segment axis, and the angle of rotation is a combination of multiple constituent rotations. However, using the technique described in Ser. No. 15/091,869, this rotation is decomposed into its axial and radial constituent rotations, which do have physiologically meaningful interpretations.

$$J \rightarrow (J_{zx}, J_y) = ((r_{zx}, x_{zx}, 0, z_{zx}), (r_y, 0, y_y, 0))$$

$J_y$ = axial rotation
$J_{zx}$ = radial rotation

The radial rotation may contain an offset due to the dissimilar Y-axis rotations in the poses of the distal and proximal body segments. That rotation is removed by rotating the radial rotation by the pose axial offsets to obtain the final radial rotation $J_{zx,f}$.

$$J_{zx,f} = ({}_E^P B'_{pE}{}^P B_d)_y J_{zx} ({}_E^P B'_{pE}{}^P B_d)_y' = (r_{zx,f}, x_{zx,f}, 0, z_{zx,f})$$

From these constituent rotations, the angular values of the joint's axial, composite radial, primary radial, and secondary radial rotations are calculated as follows.

$$\theta_a = \frac{360}{\pi} \arcsin(y_y) = \text{axial rotation angle}$$

$$\theta_{rp} = \frac{360}{\pi} \arcsin(x_{zx,f}) = \text{radial primary rotation angle}$$

$$\theta_{rs} = \frac{360}{\pi} \arcsin(z_{zx,f}) = \text{radial secondary rotation angle}$$

$$\theta_{rc} = \frac{360}{\pi} \arccos(r_{zx,f}) = \text{radial composite rotation angle}$$

FIGS. 2B-2E depict an example joint composite rotation and the constituent rotations derived from it. First, J is decomposed into the constituent rotations $J_y$ and $J_{zx}$. $J_y$ is the distal body segment's axial rotation relative to the proximal segment. Next, $J_{zx}$ is mapped into the constituent rotations $J_x$ and $J_z$ for easier visualization.

$$J_x = \left( \cos\left(\frac{\theta_{rp}}{2}\right), \sin\left(\frac{\theta_{rp}}{2}\right), 0, 0 \right)$$

$$J_z = \left( \cos\left(\frac{\theta_{rs}}{2}\right), 0, 0, \sin\left(\frac{\theta_{rs}}{2}\right) \right)$$

Note that in general:

$$J_{zx} \neq J_z J_x$$

$$J_{zx} \neq J_x J_z$$

$$J_z J_x \neq J_x J_z$$

The joint metrics can be presented to a sensor wearer, medical providers, social network, athletic coaches, etc.

Figure 5:
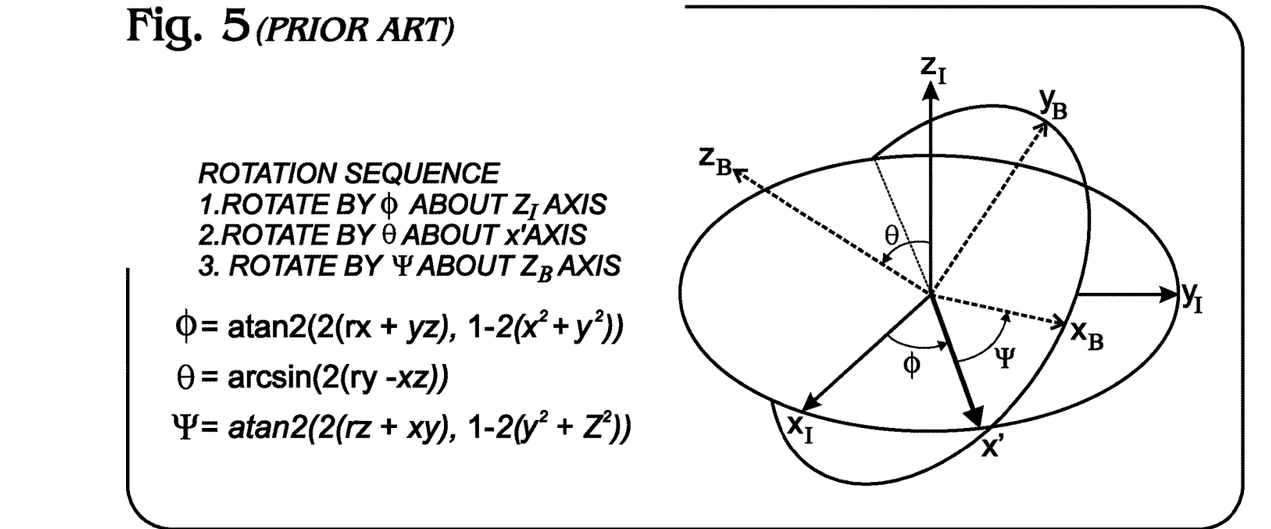
FIG. 5 is a diagram depicting a system of Euler angles (prior art).

FIG. 5 is a diagram depicting a system of Euler angles (prior art). Some conventional approaches convert quaternions to Euler angles to determine an angular representation of a rotation.

$$J \rightarrow (\varphi, \theta, \psi)$$

However, this methodology is unstable and subject to gimbal lock. Also, it does not apply a physiological model to the angular derivation, so the results can easily deviate from physiological reality.

Stable and physiologically meaningful joint rotation angles are produced by using the technique disclosed in Ser. No. 15/091,869 to decompose the joint rotation into separate axial and composite radial rotations. Also, the radial rotation can be further decomposed into primary and secondary radial rotations. The orientation of the primary radial rotation of a joint is orientation of the joint's greatest physiologically possible range of motion. For example, the knee, elbow, or neck joint's flexion and extension motions. The secondary radial rotation of a joint is perpendicular to the primary radial rotation and to the axial rotation. For example, the knee and elbow have none, and the neck has lateral bending. An example of composite radial rotation is the neck simultaneously bending both forward and to the side.

In contrast, Euler angle representations do not represent physiological rotations well. The Euler angle $\theta$ represents the composite radial rotation. The Euler angles $\varphi$ and $\psi$ do not represent any physiological rotation, as they both contribute to the axial rotation, but in general, neither one by itself is the axial rotation, and they degenerate during gimbal lock to produce highly erroneous axial rotation results.

Figure 6:
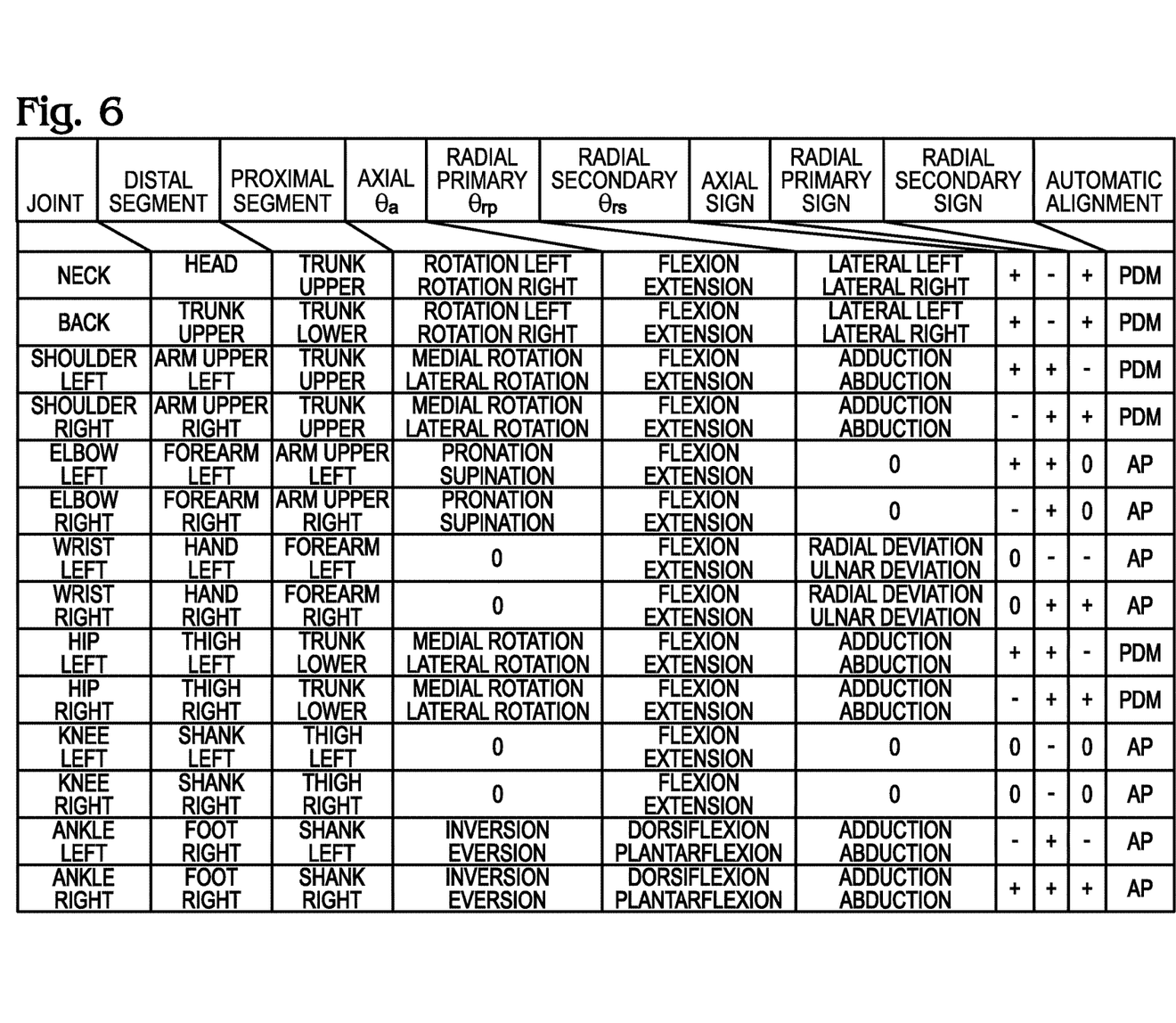
FIG. 6 is a chart listing the physiological rotations represented by the axial, primary radial, and secondary radial rotations.

FIG. 6 is a chart listing the physiological rotations represented by the axial, primary radial, and secondary radial rotations. The calculated constituent angles found using the system disclosed herein are then directly mapped to physiologically meaningful joint rotations based upon the joint being measured. The radial composite rotation is the total radial rotation, independent of the axes of the primary and secondary radial rotations.

Figure 7:
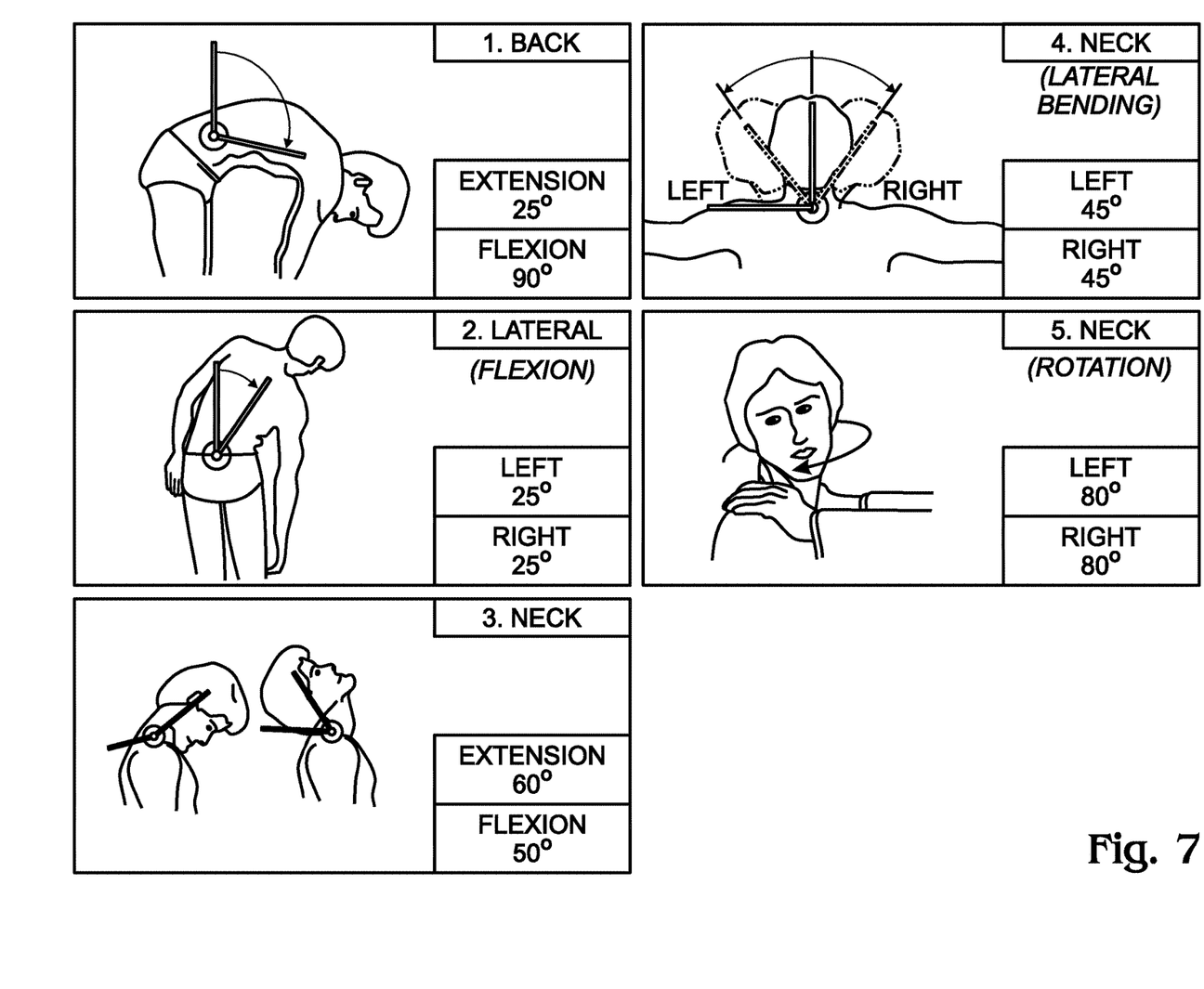
FIG. 7 is a medial diagram of joint movement.

FIG. 7 is a medial diagram of exemplary joint movements. Neck and back movements are shown. However, it should be understood that equivalent diagrams and nomenclature exists for all the joints listed in FIG. 6. Table 1 lists the medical definitions of joint rotations.

The coordinate system of Ser. No. 15/091,869, also useful in the system described herein, has each body segment's axial axis aligned with the segment's Y-axis and pointing downward for all segments except the feet, for which the Y-axis points forward. The primary radial axis is aligned with the body segment's X-axis and points to the figure's right for south and top oriented sensors, back for west oriented sensors, and front for east oriented sensors.

Medical rotations are only expressed in positive angular values, even if the joint can rotate in both directions from the 0 angle, such as the head's ability to tip both forward and backward. Instead of using positive and negative signs to distinguish between the two directions, medical convention is to use different angle names, such as flexion versus extension or adduction versus abduction. The system described herein maps signed angular values to the medical terminology as shown in Table 1.

TABLE 1

| Motion | Sign | Definition |
|---|---|---|
| Flexion | + | Bending of a joint so as to bring together the parts it connects |
| Extension | − | Straightening of a joint |
| Adduction | + | Movement that is towards the mid line of the body |
| Abduction | − | Movement that is away from the mid line of the body |
| Rotation Right | + | Movement of a bone around a longitudinal axis |

TABLE 1-continued

| Motion | Sign | Definition |
|---|---|---|
| Rotation Left | − | Movement of a bone around a longitudinal axis |
| Medial Rotation | + | Movement in which the anterior aspect of a limb turns towards the mid line |
| Lateral Rotation | − | Movement in which the anterior aspect of a limb turns away from the mid line |
| Pronation | + | Forearm rotated so that the palm of the hand faces backwards |
| Supination | − | Forearm rotated so that the palm of the hand faces forwards |
| Inversion | + | Turning inwards of the plantar aspect of the foot |
| Eversion | − | Turning outwards of the plantar aspect of the foot |
| Dorsiflexion | + | Movement of the ankle which pulls the toes and foot up towards the body |
| Plantarflexion | − | Pointing of the toes and foot away from the body |
| Radial Deviation | + | Wrist movement that is towards the mid line of the body |
| Ulnar Deviation | − | Wrist movement that is away from the mid line of the body |

The clockwise versus counter-clockwise rotational orientation for medical rotations generally flips from one side of the body to the other. For example, the right leg abducts outward in a clockwise orientation relative to a rotational axis pointing forward from the body, but the left leg abducts outward in a counter-clockwise orientation relative to that same axis. To account for this, the calculated axial, primary radial, and secondary radial rotation angles are multiplied by sign values based upon the joint being measured. FIG. 6 lists the sign values.

The user interface allows the user to select the joint being measured. Numerous selection methods are possible. Two examples are drop down menus and radio buttons. Selection of the joint automatically selects the sensors of the joint's distal and proximal body segments. FIG. 6 lists the distal and proximal body segments for each joint.

The user interface may include a representative image of the proximal and distal body segments. The proximal segment is drawn without moving. Its orientation is user selectable. The options are vertical, horizontal, or nearest axis. Nearest axis mode automatically sets the orientation to either vertical or horizontal, whichever is closest to the body segment's actual orientation. The view can be selectively set to front, back, left, right, top, or bottom. Selective setting can be accomplished by drop down menus, radio buttons, or other means. The distal segment is drawn as it moves relative to the proximal segment. The segments are drawn as multi-sided polygonal cylinders, with each side having a unique color to aid in viewing joint axial rotations. The distal segment can be drawn using either the pose uncompensated ($_p{}^dJ$) or pose compensated ($J_{pc}$) joint rotations.

Figure 8A:
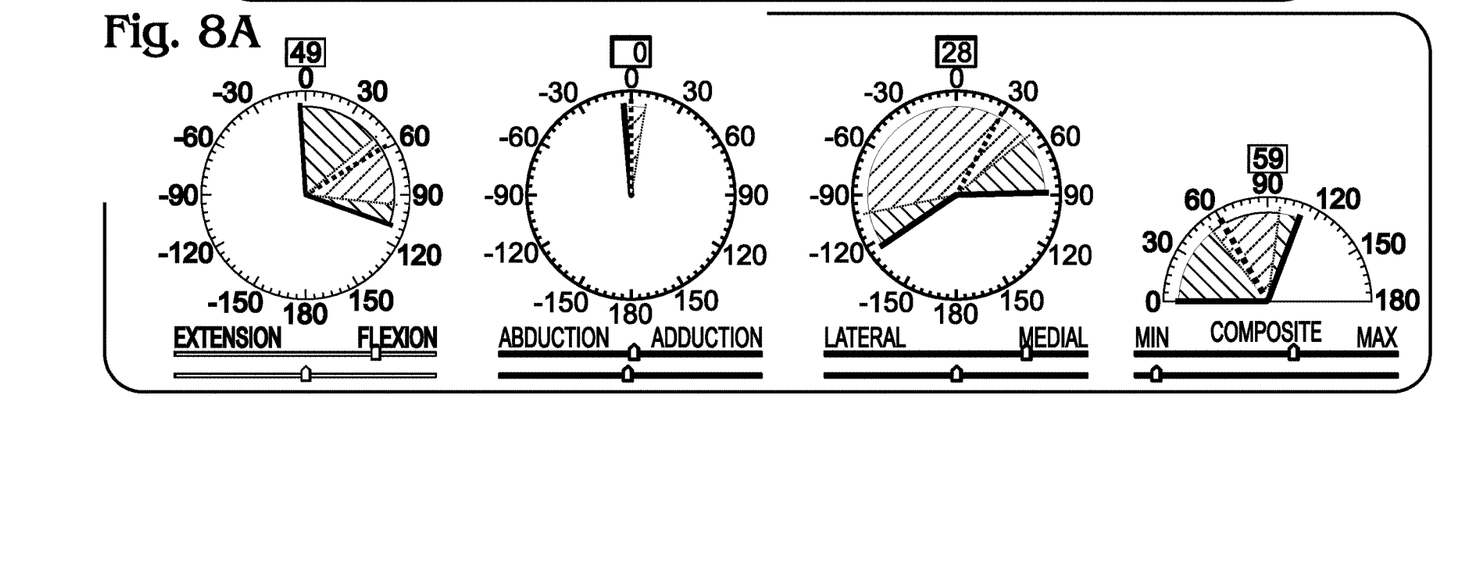
FIGS. 8A and 8B depict an exemplary user interface.
Figure 8B:
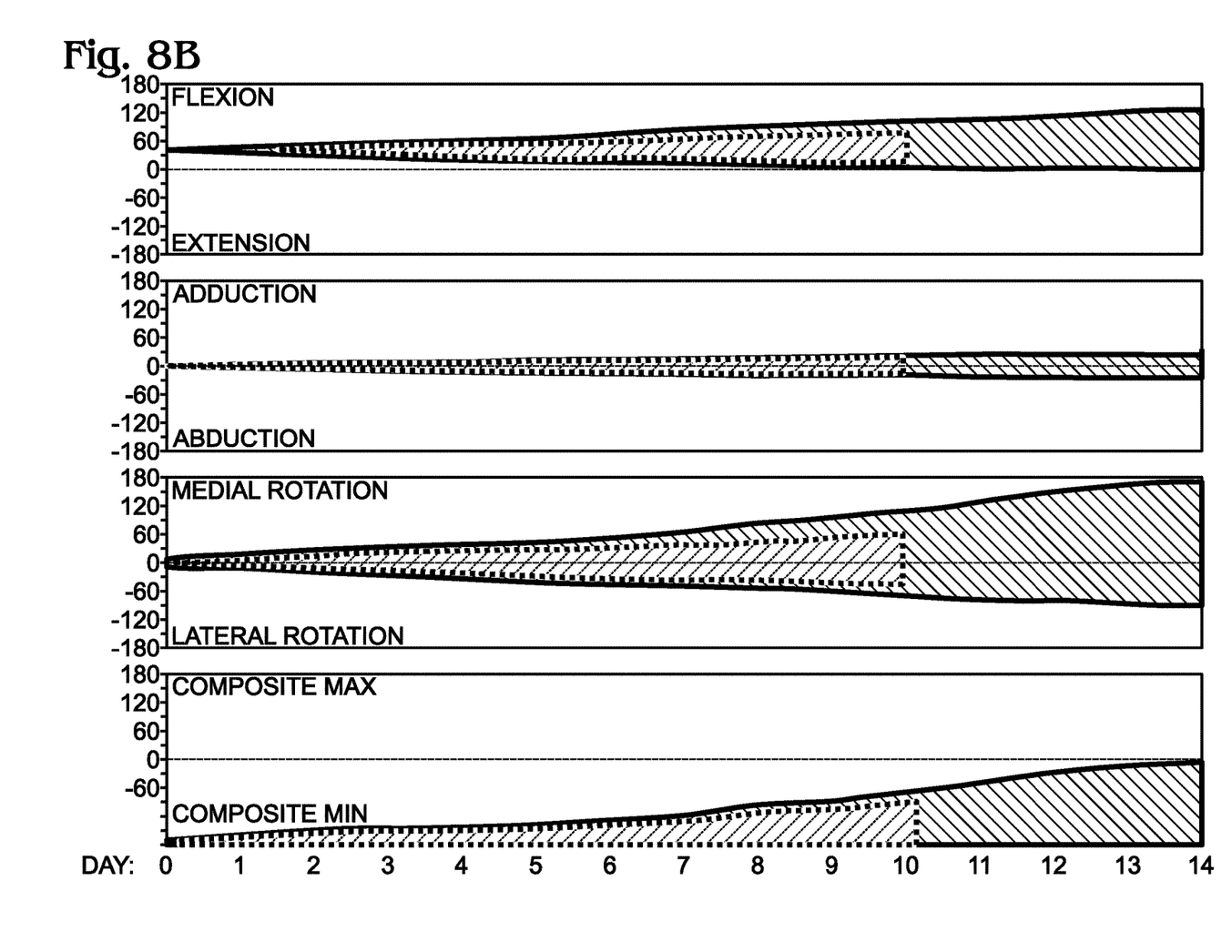

FIGS. 8A and 8B depict an exemplary user interface. The calculated rotational angles may be displayed on the user interface. There are numerous methods possible for displaying the calculated data. Each method is designed for easiest consumption of the data by both medical and non-medical personnel.

First, a numeric value is displayed for each of the four constituent angles. This provides the user with the greatest possible numeric data resolution. That value is derived from the most recent sensor readings, and can be the last calculated rotation or a filtered value of the most recent rotations, such as short term average.

Second, a dial is displayed for each of the four constituent angles. They needle graphically shows the same value as the numeric value described earlier. Each dial provides numerically labeled graticule markings for easy visual reading, and also medical rotational labels such as "Extension" and "Flexion" to clearly distinguish the context of the dial. The dial label texts automatically change based upon which joint is being measured, using the rotational angle names described in the explanation of FIGS. 2B-2E.

Each dial shows a first indication area. This area indicates the range of angles measured over an immediately previous short time period (for example 5 seconds) and spans between the minimum and maximum angles measured by the dial in that time. Then the user can quickly see the joint's most recent range of motion measured by each dial.

Each dial also shows a second indication area. This area indicates the target range of motion that the user should try to achieve. After joint surgery, a patient is often requested to slowly build up their range of motion. This indicator helps the user quickly see how well they're meeting their target RoM. The minimum and maximum angles that the target area spans can be set using two different methods. First, it can be automatically updated by a database of targets stored as a function of time. Using this method, the user always knows their current RoM targets. The database values can be set by a medical professional, athletic trainer, or other expert, and tailored to the specific user's target RoM exercise regimen. Secondly, the targets can be manually set using the slider bars located underneath each dial. This allows an easy override of the time based values. A user available setting, such as a radio button, can be used to switch between the automated and manual modes.

In addition to a target RoM being displayed on the dial, a limit RoM area can also be set and displayed in a similar manner. The limit RoM displays the absolute minimum and maximum angles that the user should not exceed. This would be used, for example, to help keep the user from over extending joints too quickly after joint surgery.

The user interface can have a "Freeze" button which stops the numeric value and dials from updating, so that a user can view a recent movement's RoM for an extended period of time while moving to a different bodily position. The Freeze button toggles between on and off.

While the dials are used for short term RoM status, the user interface may also contain graphs which display longer term RoM status, to help users track and monitor longer term trends. A separate graph is used for each of the constituent rotations. The vertical axis is the RoM displayed in degrees, and the horizontal axis is the time when the measurement occurred, displayed in minutes, hours, days, or other time units. The graphs' time bases are all aligned with each other and have mutually tracking selectable ranges.

Similar to the dials, the graphs display the user's range of motion, the RoM targets, and the RoM limits. The target and limit values are set by the database. The time base is sub-divided into smaller elements whose time width is dependent upon the range of the displayed overall time base. For example, a 14 day time base may have graticules equal to one day, with each day further divided into elements 15 minutes wide.

Each element shows the RoM for its associated period of time, indicated by the timeline displayed under the graphs. The minimum and maximum values for the user's RoM can be calculated using a number of methods. For example, they can be the minimum and maximum values that occur within the elements beginning and ending time. In another example they can be the separately low-passed filtered values of the minimum and maximum values of past times, using any desired filter configuration.

The user interface can support transport controls, allowing the user to navigate to any time location in the data and then select the desired graph time base for data viewing. This is particularly useful when data is read from a storage media as opposed to real-time. An example of transport control is sliding a cursor along the graph time base and then panning, zooming in, or zooming out the display, keeping it centered on the cursor. All data display formats, numeric, dials, and graphs update as the cursor is moved.

The sensors on either side of the joint being measured need to have their values processed by an alignment algorithm for the most accurate joint rotation calculation. Ser. No. 15/091,869 describes numerous alignment techniques. The user interface allows the user to select their alignment method of choice. An automatic alignment method selection is also available. It automatically selects one of the alignment methods described in Ser. No. 15/091,869 based upon the joint being measured, and displays that selection to the user. The constituent joint rotation relationship displayed is automatically selected based upon the joint being measured. The two methods that may be used are "Arbitrary Pose Method 3: Arbitrary pose, musculoskeletal model" (AP) and "Known Pose Method 3: Predetermined pose, unknown direction, predetermined move" (PDM). AP is the easiest method for users and is selected for joints where either the distal body segment is highly deterministic (such as hand or foot), or where the distal body segment does not have a secondary radially rotation (such as forearm or shank).

The user interface provides methods for assigning a sensor to a particular body segment. As described in Ser. No. 14/707,194, each sensor is assigned a unique ID (0 to 14). Each ID represents a unique body segment, as shown in the table of FIG. 4. Assigning a sensor to a body segment therefore reduces to updating a sensor's ID number. The user interface has a button to unassign a sensor. This button causes a message to be sent to a sensor with an existing ID, instructing that sensor to change its ID to the value 15, which is the value of an unassigned sensor. The user interface also has a button to assign a sensor. This button causes a message to be sent to a sensor that currently has and ID of 15, instructing that sensor to change its ID to the desired body segment's value, thus assigning that sensor to the new body segment.

The user interface may display the connection and calibration status for each sensor. The connection status displays whether or not data is available from that sensor. The calibration status shows whether or not the sensor has been calibrated. The user interface provides a method for calibrating a sensor. In one aspect, the user interface is as described in Ser. No. 14/742,852.

The user interface may depict an avatar image of body segments, such as the pictures shown in FIG. 4. As a user moves a sensor, the corresponding segment moves on the avatar tracks the sensor motion. This aids in identify which sensor is associated with which body segment.

The user interface may include a method for selecting a sensor based on the sensor's associated body segment and sending a message to the selected sensor instructing it to blink its status LED. This also aids in identifying which sensor is associated with which body segment.

The user interface may include a "Start" button which erases all RoM history data from the display and initiates the alignment procedure. After alignment is completed, the application begins displaying the newly received joint rotations again.

While the exemplary user interface of FIG. 8 shows only a single joint being monitored, multiple joints could be monitored. The additional joints could be shown on additional screens, or on the same screen, although the screen would become more cluttered.

To summarize, the system described in FIG. 1 may enable a graphical user interface (GUI) representing body joint range of motion as measured using IMU sensors capable of measuring their orientation relative to Earth. The conversion application 128 may supply image data to UI 132 of the physiologically modeled constituent joint rotation relationship between the proximal body segment and distal body segment as cylindrically shaped geometric forms representing body segments. For example, see FIGS. 2B-2E. Instead of simplified geometric forms, the physiologically modeled constituent joint rotation relationship between the proximal body segment and distal body segment may be presented as humanoid avatar body segments, such as shown in FIG. 7.

In another aspect, the conversion application supplies image data representing the assignment of the primary IMU sensor and secondary IMU sensor to explicit body segments, as shown for example in FIG. 4. Likewise as shown in FIG. 4, the conversion application may supply image data representing the orientation of the primary IMU sensor and secondary IMU sensor with respect to Earth.

As shown in FIG. 8, the conversion application may supply constituent joint rotation data represented as a numerical value representing an extent of rotation, a constituent joint rotation relationship over a selectable period of time, or as measured with respect to a preset rotation range indicator.

Figure 9:
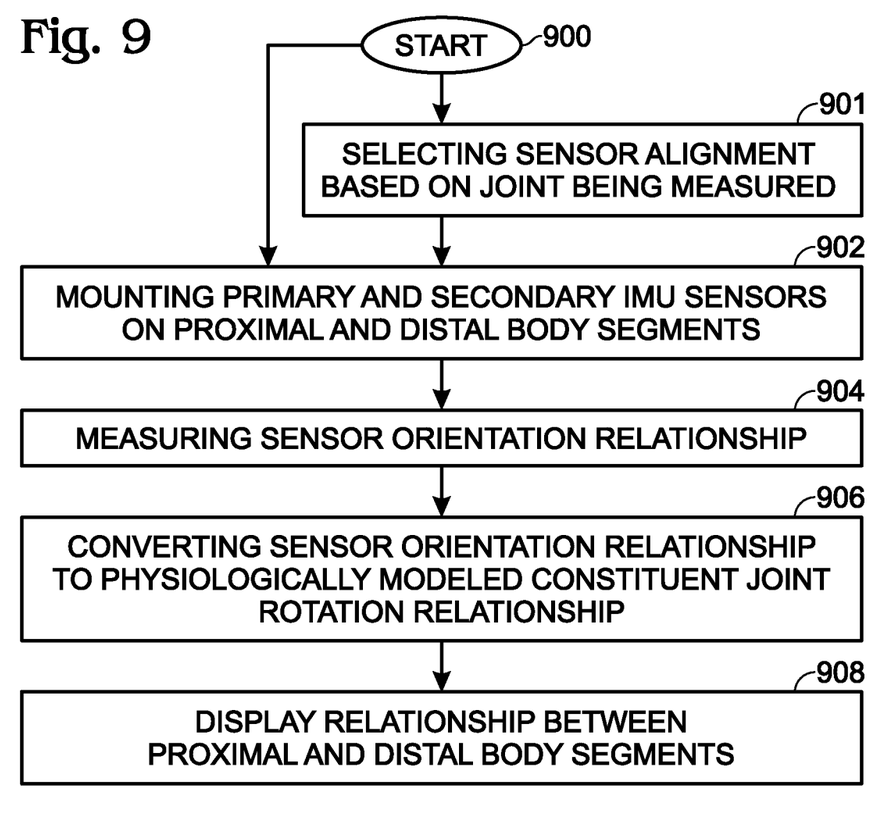
FIG. 9 is a flowchart illustrating a method for measuring body joint range of motion using IMU sensors capable of measuring their orientations relative to Earth.

FIG. 9 is a flowchart illustrating a method for measuring body joint range of motion using IMU sensors capable of measuring their orientations relative to Earth. Although the method is depicted as a sequence of numbered steps for clarity, the numbering does not necessarily dictate the order of the steps. It should be understood that some of these steps may be skipped, performed in parallel, or performed without the requirement of maintaining a strict order of sequence. Generally however, the method follows the numeric order of the depicted steps. The method starts at Step 900.

Step 902 mounts a primary IMU sensor on a proximal body segment, and a secondary IMU sensor on a distal body segment connected to the proximal body segment via a joint. Step 904 measures a sensor orientation relationship between the primary IMU sensor and the secondary IMU sensor. In one aspect, Step 904 expresses the sensor orientation relationship as a quaternion. Step 906 converts the sensor orientation relationship into at least one physiologically modeled constituent joint rotation relationship between the proximal body segment and the distal body segment. A constituent joint rotation relationship is defined in no more than two dimensions of three-dimensional space.

In one aspect, Step 901 programmatically selects a sensor alignment methodology for the primary and secondary orientation sensors based upon the body joint being measured. For example, the selection may be accomplished using a software routine.

As noted in the explanation of FIG. 2B, Step 906 may define a constituent axial axis rotation of the distal body segment measured with respect to the proximal body segment, where an axial axis intersects the joint connecting the distal body segment to the proximal body segment and is parallel to a major axis of a smallest rectangular cuboid enclosing a body segment. A major axis is a line passing through the center of two opposing sides of the cuboid that are farthest apart from each other.

As noted in the explanation of FIG. 2C, Step 906 may define a constituent radial axis composite rotation of the distal body segment measured with respect to the proximal body segment, where the radial axis intersects the joint connecting the distal body segment to the proximal body segment, is orthogonal to an axial axis of the distal body segment, and is orthogonal to an axial axis of the proximal body segment.

As described in the explanation of FIGS. 2D and 2E, Step 906 may respectively define a constituent primary radial rotation and a constituent secondary radial rotation. The primary radial rotation represents a first angle measured with respect to a first axis aligned with the radial axis of maximum possible physiologically possible radial rotation. The secondary rotation represents a second angle measured with respect to a second axis orthogonal to the first axis and the axial axis.

In one aspect, Step 908 displays, on a UI, the physiologically modeled constituent joint rotation relationship between the proximal body segment and the distal body segment. In one variation, the constituent joint rotation relationships are displayed as numerical values representing an extent of rotation. In another aspect, Step 908 maps at least one constituent rotation relationship to a physiologically defined joint rotation, as shown for example in FIG. 6.

A system and method have been provided for measuring the range of motion of joints connecting adjacent body segments using IMU sensors. Examples of particular algorithms and hardware units have been presented to illustrate the invention. However, the invention is not limited to merely these examples. Other variations and embodiments of the invention will occur to those skilled in the art.

I claim:

1. A method for measuring body joint range of motion by a joint rotation measurement device that communicates with inertial measurement unit (IMU) sensors capable of measuring the IMUs' orientations relative to Earth, the method comprising:
   receiving, at the joint rotation measurement device, orientation data from a primary IMU sensor mounted on a proximal body segment and a secondary IMU sensor mounted on a distal body segment connected to the proximal body segment via a joint;
   measuring, at the joint rotation measurement device, a sensor orientation relationship between the primary IMU sensor and the secondary IMU sensor using the orientation data received from the primary and secondary IMU sensors; and
   converting, by a conversion application stored at a memory of the joint rotation measurement device, the sensor orientation relationship into at least one physiologically modeled constituent joint rotation relationship between the proximal body segment and the distal body segment, where a constituent joint rotation relationship is defined in no more than two dimensions of three-dimensional space,
   wherein converting the sensor orientation relationship into the physiologically modeled constituent joint rotation relationship includes defining a constituent axial axis rotation of the distal body segment measured with respect to the proximal body segment, where an axial intersects the joint connecting the distal body segment to the proximal body segment and is parallel to a major axis of a smallest rectangular cuboid enclosing a body segment, and where a major axis is a line passing through the center of two opposing sides of the cuboid that are farthest apart from each other.

2. The method of claim 1, wherein measuring the sensor orientation relationship includes expressing the sensor orientation relationship as a quaternion.

3. A method for measuring body joint range of motion using by a joint rotation measurement device that communicates with inertial measurement unit (IMU) sensors capable of measuring the IMUs' orientations relative to Earth, the method comprising:
   receiving, at the joint rotation measurement device, orientation data from a primary IMU sensor mounted on a proximal body segment and a secondary IMU sensor mounted on a distal body segment connected to the proximal body segment via a joint;
   measuring, at the joint rotation measurement device, a sensor orientation relationship between the primary IMU sensor and the secondary IMU sensor using the orientation data received from the primary and secondary IMU sensors; and
   converting, by a conversion application stored at a memory of the joint rotation measurement device, the sensor orientation relationship into at least one physiologically modeled constituent joint rotation relationship between the proximal body segment and the distal body segment, where a constituent joint rotation relationship is defined in no more than two dimensions of three-dimensional space,
   wherein converting the sensor orientation relationship into the physiologically modeled constituent joint rotation relationship includes defining a constituent radial axis composite rotation of the distal body segment measured with respect to the proximal body segment, where the radial axis intersects the joint connecting the distal body segment to the proximal body segment, is orthogonal to an axial axis of the distal body segment, is orthogonal to an axial axis of the proximal body segment, where an axial axis intersects the joint connecting the distal body segment to the proximal body segment and is parallel to a major axis of a smallest rectangular cuboid enclosing a body segment, and where a major axis is a line passing through the center of two opposing sides of the cuboid that are farthest apart from each other.

4. The method of claim 3, wherein defining the radial axis composite rotation comprises defining a constituent primary radial rotation and a constituent secondary radial rotation, where the primary radial rotation represents a first angle measured with respect to a first axis aligned with the radial axis of maximum possibly physiologically possible radial rotation, and the secondary rotation represents a second angle measured with respect to a second axis orthogonal to the first axis and the axial axis.

5. The method of claim 1 further comprising:
   displaying, on a user interface (UI) displayed on a display of the joint rotation measurement device, the physiologically modeled constituent joint rotation relationship between the proximal body segment and the distal body segment.

6. The method of claim 5, wherein the displaying the physiologically modeled constituent joint rotation relationship includes displaying the constituent joint rotation relationship as a numerical value representing an extent of rotation.

7. The method of claim 5, wherein displaying the physiologically modeled constituent joint rotation relationship includes mapping at least one constituent rotation relationship to a physiologically defined joint rotation.

8. The method of claim 1 further comprising:
   programmatically selecting a sensor alignment methodology for the primary and secondary orientation sensors based upon the body joint being measured.

* * * * *